United States Patent
Neyer et al.

(10) Patent No.: US 6,962,658 B2
(45) Date of Patent: Nov. 8, 2005

(54) VARIABLE FLOW RATE INJECTOR

(75) Inventors: David W. Neyer, Castro Valley, CA (US); David J. Rakestraw, Livermore, CA (US); Jason E. Rehm, Alameda, CA (US)

(73) Assignee: Eksigent Technologies, LLC, Livermore, CA (US)

( * ) Notice: Subject to any disclaimer, the term of this patent is extended or adjusted under 35 U.S.C. 154(b) by 258 days.

(21) Appl. No.: 10/441,640

(22) Filed: May 20, 2003

(65) Prior Publication Data

US 2004/0232080 A1 Nov. 25, 2004

(51) Int. Cl.$^7$ .............................................. B01D 15/08
(52) U.S. Cl. .................... 210/198.2; 210/656; 210/101; 210/143
(58) Field of Search ................................ 210/635, 656, 210/659, 101, 143, 198.2; 422/70; 436/161

(56) References Cited

U.S. PATENT DOCUMENTS

| | | | |
|---|---|---|---|
| 5,236,847 A | | 8/1993 | Satake et al. |
| 5,789,258 A | | 8/1998 | Drinkwine et al. |
| 5,827,426 A | | 10/1998 | Fujii et al. |
| 5,942,093 A | * | 8/1999 | Rakestraw et al. ......... 204/450 |
| 6,290,909 B1 | * | 9/2001 | Paul et al. .................... 422/70 |
| 6,492,184 B1 | | 12/2002 | Petro et al. |
| 6,833,068 B2 | | 12/2004 | Paul et al. |
| 2002/0146840 A1 | | 10/2002 | Hage et al. |
| 2003/0064008 A1 | | 4/2003 | Hage et al. |

OTHER PUBLICATIONS

Foster, Marc D., Performance of Experimental Sample Injectors for High–Performance Liquid Chromatography Microcolumns, Journal of Chromatography (2000), p. 231–241.
Notification of Transmittal of the International Search Report and the Written Opinion of the International Searching Authority (PCT–US04/15838).

* cited by examiner

Primary Examiner—Ernest G. Therkorn
(74) Attorney, Agent, or Firm—Sheldon & Mak; Jeffrey G. Sheldon

(57) ABSTRACT

A variable flow rate injector provides accurate, precise, and reproducible injection volumes that have low dispersion. The invention is particularly well-suited for HPLC injection volumes <500 nL but can be used to inject larger volumes and in different applications as well. Injections are performed at a first flow rate and separations are performed at a second flow rate. For improved HPLC system performance, the first flow rate is less than the second flow rate. The injector uses a variable flow rate fluid supply that allows rapid switching between flow rates desired for injection and flow rates desired for separations.

10 Claims, 5 Drawing Sheets

VARIABLE FLOW RATE INJECTOR

CROSS REFERENCE TO RELATED APPLICATIONS

This application is related to U.S. patent application Ser. No. 10/246,284, filed Sep. 17, 2002, which is a continuation-in-part of U.S. patent application Ser. No. U.S. 2002/01953444 filed May 24,2002, with a continuation-in-part of U.S. patent application No. U.S. 2002/0189947 filed Aug. 29, 2001 that claims the benefit of U.S. Provisional application No. 60/298,147 filed June 13, 2001. the entire disclosures of which are incorporated by reference in their entirety for any and all purposes.

BACKGROUND

High performance liquid chromatography (HPLC) is a technique that has been used for many years as a means of separating, identifying, purifying and quantifying components of often complex mixtures. HPLC is an important tool used by biotechnological, biomedical, and biochemical research as well as in the pharmaceutical, cosmetics, energy, food, and environmental industries.

Conventional HPLC typically is performed using chromatographic columns with inside diameters (I.D.'s) in the range of about 2–10 mm, 4.6 mm columns being a common standard. Microcolumn liquid chromatography ("LC"), which is the most widely accepted term to describe liquid chromatography using packed columns having I.D.'s of 2mm or less, is gaining in popularity. Advantages of microcolumn LC include the ability so analyze smaller sample volumes, reduction of solvent usage, and enhanced mass sensitivity.

Due to their relatively large volume, sample injection systems developed for conventional HPLC systems are inadequate for use in microcolnum LC systems. Sample volume requirements for microcolumn LC relative to conventional HPLC can be determined by considering a constant sample volume to column volume ratio. For example, a direct scaling of injection volumes indicates that a 10 $\mu$L sample injection into a 4.6 mm i.d. conventional HPLC column would be equivalent to 43 nL, 4.7 nL and 1.2 nL sample injections into 300 $\mu$m, 100 $\mu$m and 50 $\mu$m i.d. nanobore HPLC columns, respectively.

Injection valves and injection methods have been developed in an attempt to meet the demands of volume injections of 500 nL and less. See, for example, those disclosed in Vissers, J. P. C., Arnoud, H. R., Ursem, M. and Chervet, J. P., "Optimised injection techniques for micro and capillary liquid chromatography", *J. of Chrom A,* 746, p 1, (1996); Bakalyar, S. R., Phipps, C., Spruce, B. and Olsen, K., "Choosing sample volume to achieve maximum detection sensitivity and resolution with high-performance liquid chromatography columns of 1.0, 2.1 and 4.6 mm I.D.", *J. Chrom. A,* 762, p 167, (1997); Foster, M.D., Arnold, M. A., Nichols, J. A. and Bakalyar, S. R., "Performance of experimental sample injectors for high-performance, liquid chromatography microcolumns", *J. Chrom. A,* 869, p 231, (2000). Others include commercially available valves from companies such as VICI Valco Instruments, Rheodyne and Upchurch Scientific. Valve designs include both external and internal sample loops. Injection volumes of less than 100 nL are typically achieved using valves with internal sample loops where a groove in the rotor serves as the loop. Larger injection volumes can be achieved with either internal loops or external loops connected to the valve ports.

In conventional HPLC systems, the resolution and efficiency of the separation have been primarily determined by the performance of the column itself. In contrast to conventional HPLC systems, the resolution and separation efficiency of microscale HPLC systems is often determined by band-broadening from the sample injector, connection tubing and detector cell.

The band-broadening due to the instrumental components as well as the column is called dispersion and is characterized by the variance of the peak shape. The ideal injection (square pulse) will introduce a variance, $\sigma^2$, of $\sim V^2/12$, where V is the injection volume. In practice, this ideal injection performance has not been demonstrated for injection volumes of <500 nL and the sample is contained in a volume much larger than the ideal square pulse.

In addition to minimizing the variance, microcolumn LC systems must have the ability to quantitatively inject small sample volumes. Although internal loop injectors can directly provide for injection volumes as small as 10 nL, the absolute accuracy and consistency from loop to loop are poor.

As the injection volumes become smaller, quantitative injections become more difficult. This difficulty is reflected in the literature as well as product specifications of commercial instruments. For example, the specifications for the relative standard deviation on the Agilent 1100 HPLC system using a conventional injection size of 5 $\mu$L is 6 times better than for the Agilent 1100 CapLC using injection volumes of 0.2–1.0 $\mu$L. No specification is given for smaller injection volumes. Typical repeatability for peak areas in microscale LC are in the 2–6% range compared to 0.5% for conventional size systems.

Accordingly, there is a need in the art for an HPLC injector and a method for injecting a sample fluid into a separation column that provides the ability to reduce injection variance and maintain very accurate and precise injection volumes.

SUMMARY

The present invention provides an injection system particularly suitable for HPLC systems, that satisfies this need. According to the present invention, a method for injecting a sample into a device such as a microcolumn comprises placing the sample into a sample injection zone, moving at least a portion of the placed sample from the sample injection zone into the device with a working fluid flowing at a first flow rate, and thereafter, introducing the working fluid into the device at a second flow rate. The first flow rate is at least 25% less than the second flow rate. Thus, sample is introduced at a rate lower than the rate at which the working fluid is introduced during the working portion of the process. This lower rate reduces sample dispersion.

Typically the volume of the sample injected is less than about 500 nL. Preferably the time delay between injecting the sample into the device and increasing the flow rate of the working fluid is less than about five seconds, and more preferably less than about one second. The first flow rate is typically from 0.01 to about 0.75 of the second flow rate. Typically, the second flow rate for a microcolumn is less than about 100 $\mu$L per minute.

When the sample is injected into the device, the working fluid can move substantially all of the sample, or only a portion of the sample.

Hardware for practicing this method can comprise a variable flow rate source for the working fluid, a sample source, a valve in fluid communication with the sample source, and a controller. The valve has a sample load position and a sample inject position. In the sample load position, sample is loaded for later injection. In the sample inject position, a coded sample is injected by the working fluid into the device. The controller is in communication with the working fluid source for controlling the flow rate of the working fluid.

The variable flow rate working source can be an electrokinetic pump, and can include an electroosmotic flow controller or a variable pressure source. More than one working fluid can be used. A control system can be provided that maintains the working fluid flow rate set against a target flow rate.

DRAWINGS

These and other features, aspects and advantages of the present invention will become better understood with regard to the following description, appended claims, and accompanying drawings where:

FIG. 1 schematically illustrates a first HPLC system having a variable flow rate injector in accordance with the present invention.

FIG. 2 schematically illustrates a second HPLC system having a variable flow rate injector in accordance with the present invention.

DESCRIPTION

The present invention is directed towards an injector and method that can provide accurate, precise, and reproducible injection volumes that have low dispersion. The invention is particularly well-suited for HPLC injection volumes <500 nL but can be used to inject larger volumes and in different applications as well.

Figure 1:
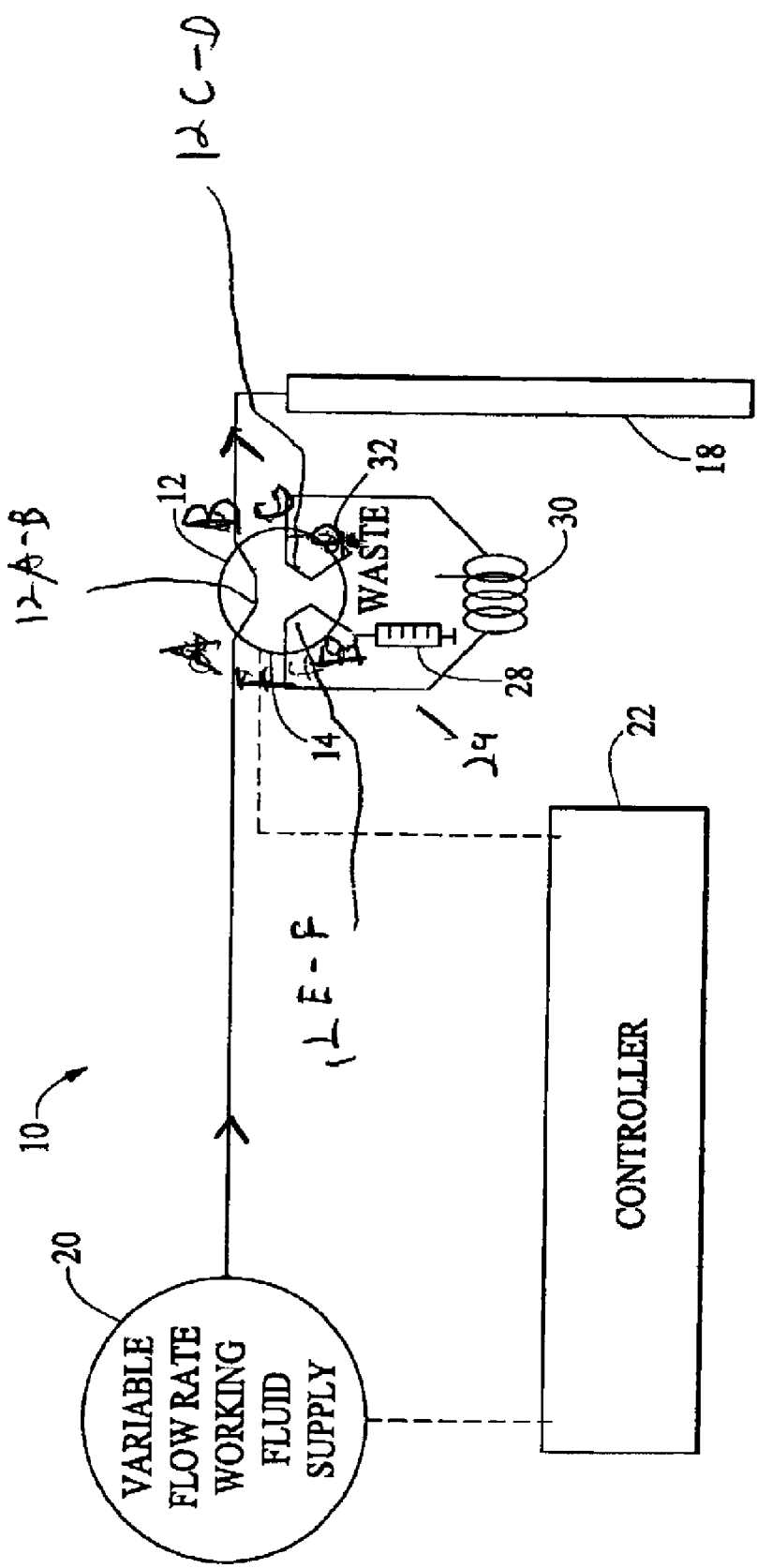

A system 10 having features of the present invention is shown in FIG. 1. An injection valve 12 has a sample load position 14 and a sample inject position 16. In FIG. 1 the injection valve 12 is in the sample load position 14. The valve 12 has six ports, ports A–F, as shown in FIG. 1, with port A at about a 10 o'clock position, and the other ports being substantially equally spaced apart from each other. The valve 12 has three internal flow paths, also referred to as channels, 12A–B, 12C–D, and 12E–F between ports A and B, C and D, and E and F, respectively.

A device such as a separation column 18 is in fluid communication with the injection valve 12. A variable flow rate working fluid source 20 providing a working fluid that is in fluid communication with the injection valve 12 and the separation column 18. When the injection valve 12 is in the sample load position 14, the working fluid flows through flow path 12 A–B into the separation column 18. A sample source provides a sample to be injected into the column 18. The sample can be injected by a syringe 28 into a sample injection zone such as a loop 29 that includes a sample retention coil 30. The loop 29 is external to the valve 12.

Figure 2:
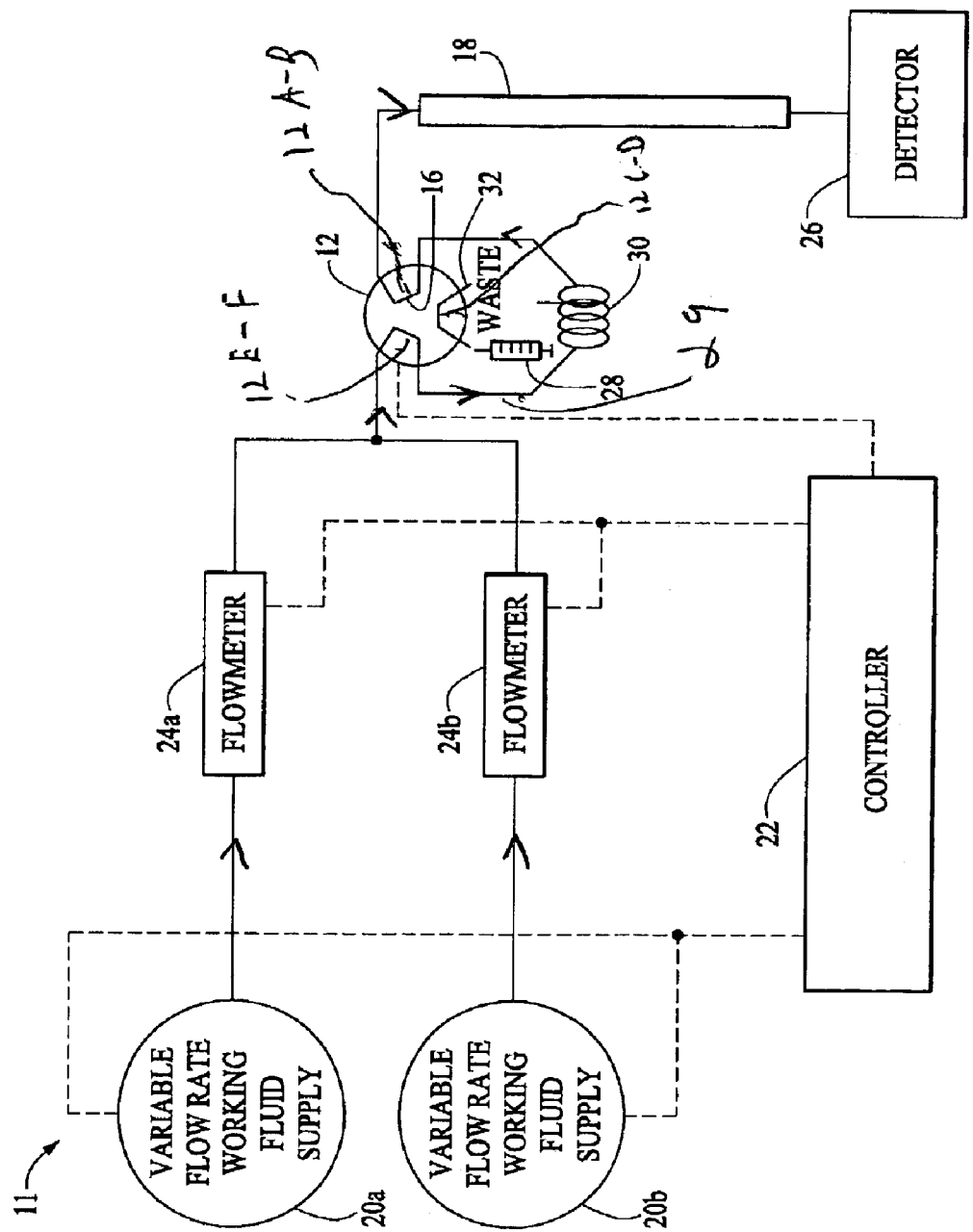

When the injection valve is in the sample injection position 16, as shown in FIG. 2, the working fluid displaces a volume of sample solution from the injection valve 12 so that the volume of sample solution enters the separation column. As shown in FIG. 2, working fluid flows through valve channel 12E–F, into the loop 29 and through coil 30, thereby displacing at least a portion of any placed sample, and then through valve channel 12A–B and into the column 18.

While a typical six-port injection valve is shown in FIGS. 1 and 2, many other configurations of injection valves which have different numbers and positions of ports and channels are common and can be used. Rather than using a loop external to the valve as the sample injection zone, one or more of the internal valve channels (similar to channel 12E–F and/or channel 12A–B) can be used.

A controller 22 is in communication with the variable flow rate pressure source 20 and the injection valve 12 for controlling the flow rate of the working fluid and controlling the position of the valve 12. When the working fluid displaces the sample solution from the injection valve 12, the working fluid flows at a first flow rate. After the working fluid displaces at least a portion of the sample, the working fluid flows at a second flow rate. The first flow rate is different from the second flow rate.

FIG. 2 illustrates an HPLC system embodying features of the invention. The variable flow rate working fluid supply 20 comprises two variable flow rate working fluid supplies 20a and 20b. The flow rate of each fluid supply is measured by a respective flowmeter 24a or 24b that is in communication with the controller 22. The controller 22 compares the measured flow rates of each of the working fluids with a respective desired or target flow and adjusts the respective variable flow rate working fluid supply 20a or 20b so that the respective working fluid flows at about the target flow rate and so that the working fluid flows through the injection valve 12 at about the target flow rate. The HPLC system 11 shown in FIG. 2 also includes a detector 26 for detecting analytes in fluid after passing through the separation column 18.

The working fluids are mixed after exiting the flowmeters 24a and 24b and before passing through the injection valve 12. Mixing can occur via diffusion or via passive or active devices. Ideally, the mixed fluids only need to flow through a minimal volume, the delay volume, 100 nL for example, to the injection valve 12 so that changes in mixture composition are accurately represented, with little time delay, in the fluid passing through the injection valve. If desired, one or both fluids can be used for sample injection, and one or both can be used for running the column 18.

Preferably, the controller 22 can compensate for changes in the working fluids or mixtures that affect the flow rates. These may include, for example, viscosity changes or volumetric changes upon mixing. Hence, preferably, the controllers 22 can obtain the physical properties of the fluid such as composition, temperature and pressure. For example, the composition and mixing ratio of both fluids can be input to the controller; the flowmeter can measure the pressure; and a thermocouple in communication with the controller can take the temperature measurement. Alternatively, the system can be temperature controlled and the temperature communicated to the controller.

Because the flow rate is measured and the measured flow rate is used to adjust the variable pressure fluid supply as opposed to adjusting the mechanical displacement of a pump element, e.g., a lead-screw driven piston, so that it is proportional to a desired flow rate, the system is capable of delivering fluid predictably and reproducibly even at low flow rates and even if there is check valve leakage, pump seal leakage, flexing and creep of mechanical seals, thermal expansion of components and compression of the working fluid.

Preferably the system has a response time of less than one second so that when the measured flow rate does not substantially equal the target flow rate, the actual flow rate is quickly adjusted to substantially equal the desired flow rate within one second, wherein substantially equal means within 5%.

The injection valve 12 can be any injection valve known in the art, for example commercial rotary valves such as those available from Rheodyne, Valco Instruments, or Upchurch Scientific, or microfluidic injectors such as those disclosed in U.S. Pat. No. 6,290,909 (which is incorporated hereby reference) and U.S. patent publication No. 2002/0194909 (incorporated herein by reference). Sample loading is effected with the syringe introducing sample into valve port E for flow through valve flow path 12E–F, and into the sample loop 29 including into the coil 30. To be certain that sufficient sample is provided, there is a waste receptacle at valve port D, wherein valve channel 12C–D is in communication with the waste receptacle. By introducing sufficient sample into the sample injection zone that sample appears at waste insures that sufficient sample is provided for injection into the column 18.

The variable flow rate working fluid supply 20 can be of any type known in the arts or developed in the future including but not limited to: direct electrokinetic pumps, such as those disclosed in U.S. Pat. No. 5,942,093, which is incorporated herein by reference for any and all purposes; electrokinetic flow controllers, such as those disclosed in U.S. patent application Ser. Nos. 09/942,884 and 10/155,474 which are incorporated herein by reference for any and all purposes; electropneumatic pumps with and without hydraulic amplifiers, such as those described in U.S. patent application Ser. No. 10/246,284, which is incorporated herein by reference for any and all purposes; and mechanically actuated pumps. Although many current designs of positive displacement pumps, such as lead-screw driven pumps, do not have the performance to address the precision at the low flow rate ranges, they may be used in active flow rate feedback in future designs. When more than one variable flow rate working fluid supplies are used, they need not be the same. Preferably the variable flow rate working fluid supply 30 is continuously variable, can provide flow rates in the range of 1 nL/minute to 100 $\mu$l/minute into back pressures of up to 5000 psi or higher, and have a response time of seconds or less, thus allowing rapid changes in flow rates.

The controller 22 can be any controller known in the art, for example, a PID servo-loop controller, and can be constructed using discrete analog circuits, discrete digital circuits, dedicated microprocessors or a computer, for example.

The working fluid can be the mobile phase in an HPLC system, for example or any other fluid. The sample solution can contain analytes or be any fluid. The term "sample" is used herein broadly to refer to any material which it may be desired to inject into a device. For example for a column such as a microcolumn the sample can contain one or more compounds that are to be separated, analyzed, and/or reacted, where the compound(s) are known or unknown.

The flowmeter 24 may be of any type known in the art including but not limited to: determining flow rate from measured pressure difference across a known flow conductance; a Coriolis flowmeter as disclosed in P. Enoksson, G. Stemme and E. Stemme, "A silicon resonant sensor structure for Coriolis mass flow measurements," J. MEMS vol. 6 pp. 119–125 (1997); a thermal mass-flowmeter; a thermal heat tracer as disclosed in U.S. Pat. No. 6,386,050; and an optical flowmeter, for example, a Sagnac interferometer as disclosed in R. T. de Carvalho and J. Blake, "Slow-flow measurements and fluid dynamics analysis using the Fresnel drag effect," Appl. Opt. vol. 33, pp. 6073–6077 (1994). Preferably the flowmeter 24 provides accurate and precise measurements of flow rates in the range of 100 $\mu$L/min to 10 nL/min, typical flow rates for microcolumns. It is further preferable that the flowmeter 24 provide a signal that is continuous over all desired flow rates including fluid flow in both directions. It is further preferable that the signal bandwidth of the flowmeter 24, i.e. the frequency corresponding to the minimum time between meaningful readings, is faster than one Hertz, and more preferable faster than 10 Hertz.

These objectives can be accomplished by a flowmeter comprising a metering capillary having a sufficiently long length and a sufficiently small inner diameter so that the pressure drop across the metering capillary is at least 5% of the input pressure to the capillary at the desired flow rate, and a pressure sensor for measuring the pressure drop across the metering capillary, wherein the input pressure is the pressure of the fluid as it enters the capillary. One or more pressure sensors can be used to measure the pressure drop across the capillary directly or by measuring the pressure at both ends of the capillary and subtracting one pressure measurement from the other. The pressure sensor can be a pressure transducer. Minimizing the volume and size of the pressure transducers to 10 microliters, for example, allows for rapid response of the flowmeter since the compressibility of the fluid and the deflection of the pressure transducer membrane contribute to the time response.

For example, a pressure drop of about 450 psi through a 10 cm long and 10 micron ID capillary indicates a flow rate of about 500 nL/min for water at room temperature. Similar relations can be determined for other fluids, geometries, pressure differences, and lengths of tubing using the well known Darcy's law for pressure driven flow. Accurate flow rate measurements also require knowledge of the fluid viscosity.

There are at least two fill methods of using an HPLC system having features of the present invention, a complete fill method and a partial fill method. In the complete fill method, while the injection valve 12 is in the load position 14, an amount of sample in excess of what is needed for injection is inserted into the sample loop 29. The amount of sample needed to uniformly and completely fill the sample loop 29 depends on many parameters including, the geometry of the sample loop, connection ports, volumetric flow rate during loading, viscosity of the sample solution and the diffusion constants of the components in the next sample. The first flow rate of the working fluid is established. This is the flow rate at which the sample solution is displaced from the sample loop. The valve is actuated into the run position for a time great enough to displace a desired amount of the placed sample. Timed injections (also referred to as moving, temporary, or time slice injections) take advantage of either pneumatic or electronic valve actuation, for example, that switches the injection valve 12 into the run position 16 for a desired period of time to transfer a desired volume of the sample solution out of the sample loop 29. When the injection valve 12 is in the run position 16, the desired volume of the sample solution is displaced from the sample loop 29 by the working fluid. This injection method requires the first flow rate to be stable and precise enough to allow a known and repeatable volume of sample to be injected. The desired volume is usually only a portion of the placed sample 12. The injection valve 12 then switches back to the load position 14. This method often allows the dispersion in the trailing boundary of the sample to be reduced.

The flow rate of the working fluid (second flow rate) desired for separation is preferably established before the sample enters the separation column. Because the connection volume between the injector and the separation column is preferably kept to a minimum, the second flow rate is preferably established rapidly, preferably in less than about five seconds, and more preferably in less than about one second. After passing through the injection valve 12, the sample solution can enter the separation column 18 at the second flow rate. After the injection valve 12 is switched back to the load position 14, more sample solution can be inserted into the sample loop to flush out the sample loop 29, forcing all of the working fluid out of the sample loop and through the fluid outlet 32 into waste and refilling the sample loop with the sample solution.

In the partial fill method, less than the amount of sample needed to fill the loop 29 is used. While the injection valve 12 is in the load position 14, a predetermined amount of sample solution is metered into the sample loop 29. It is preferable that none of the sample solution reaches the far end of the sample loop 29 during loading to ensure that the metered sample volume is fully contained in the sample loop. When the injection valve 12 is switched into the run position 16, the entire volume of the sample loop 29 is displaced by the working fluid. After passing through the injection valve 12, the sample solution can enter the separation column 18. The injection valve 12 can be switched back to the load position 14 and the process can be repeated.

These methods are applicable to any sample volume, including when the volume of the sample solution displaced from the injection valve 12 is less than approximately 500 nL. When either method is used, one flow rate of the working fluid is used to inject the sample solution and a second greater flow rate of the working fluid is used during separation of the sample solution. When the sample solution is being neither injected nor separated, the flow rate of the working fluid is preferably changed from the first flow rate to the second flow rate in a prescribed and reproducible method so that the elution times of the separated sample components are reproducible. This may be a rapid step change in the flow rate or a more gradual ramp from the first flow rate to the second flow rate flow rate. The flow rate of the working fluid can switch from the first flow rate to the second flow rate at any time between injection and separation and can switch from the second flow rate to the first flow rate at any time after separation of the sample solution and before injection of the next volume of sample solution. Both flow rates are preferably less than approximately 100 $\mu$L/min. For reduced dispersion and optimal separation the first flow rate is preferably less than the second flow rate.

The device 18 need not be a separation column, but can be another component, such as a microfluidic reaction chamber or detector.

The controller 22 can cause the flow rate to switch from the first flow rate to the second flow rate in less than approximately five seconds from the time that the injection valve 12 switches from the run position 16 to the load position 14. Alternatively, the switching of the flow rates can be delayed from the valve switching by a predetermined time or have other triggers, such as an optical, electronic, or electrochemical sensor.

Typically the first flow rate is about 25% less than the second flow rate for minimizing dispersion of the injected sample. For example, the first flow rate can be from about 1 to about 75% of the second rate, and preferably from about 10 to about 75% of the second flow rate. As an example, for an HPLC system, the first flow rate use for injection can be about 100 nanoliter per minute, and the second flow rate of working fluid used for separation can be 10 microliters per minute.

The ability to use different flow rates for injection and separation allows both processes to be optimized independently. The benefits of this invention can be illustrated by considering the case of optimizing injection and separation flow rates for a 300 $\mu$m i.d. separation column 18. A flow rate of approximately 3–4 $\mu$L/minute is typical for optimized separation performance. Injection volumes of less than about 50 nL (assuming ideal injections, i.e. a square pulse) may be desired to minimize dispersion effects for certain applications. In particular HPLC separations with weakly retained compounds including size exclusion chromatography and other isocratic separations may require small injection volumes with minimal dispersion. As an example, the total extra column variance, including the injector, detector and connecting tubing, for a 150 mm long column expected to yield 10,000 theoretical plates should be kept below about 370 nL$^2$ (or 10% of the variance produced by the column). The amount of dispersion introduced by increased flow velocity depends on detailed geometries of the loop and valve ports, solvents and analytes.

EXAMPLE 1

Figure 3:
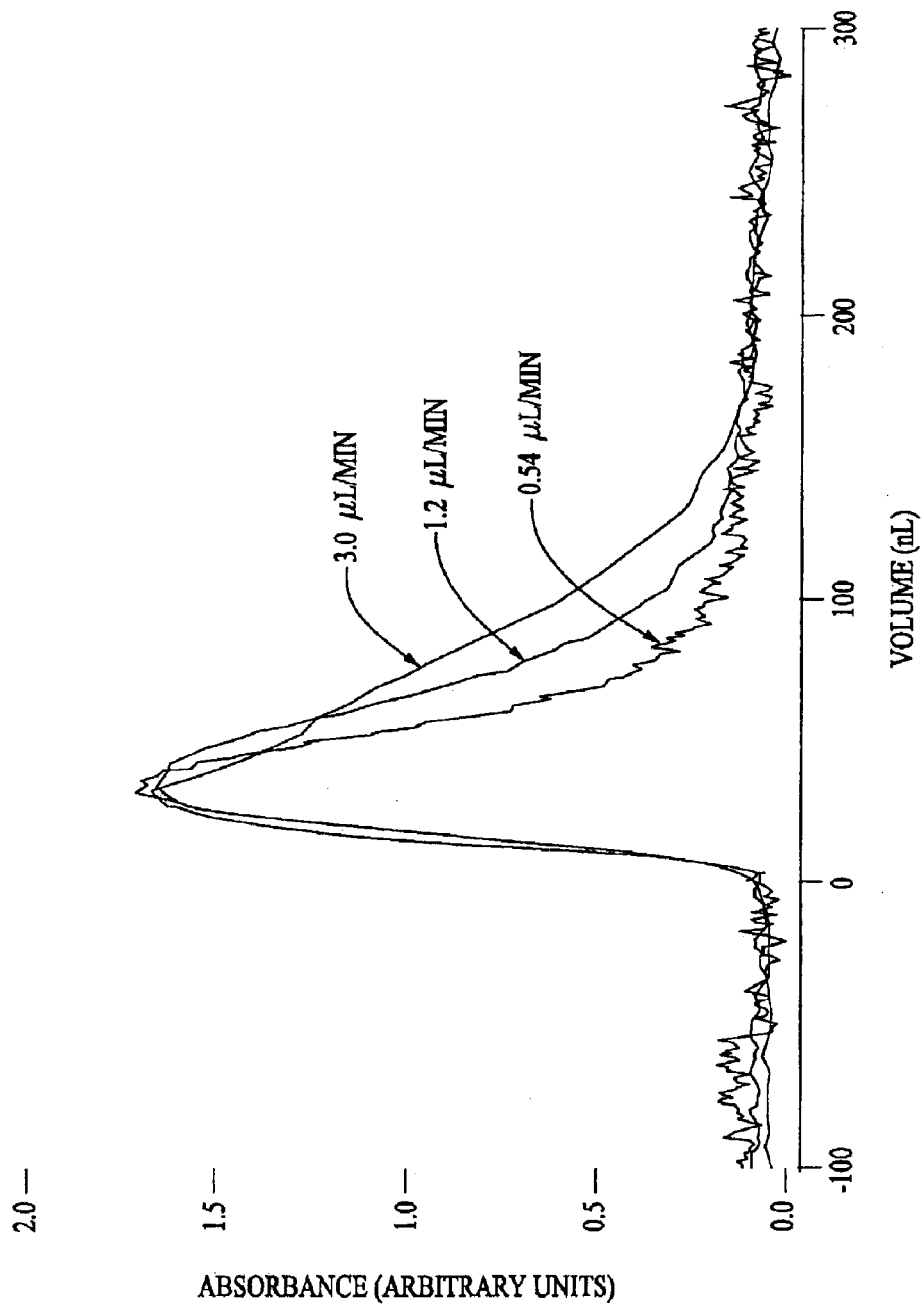
FIG. 3 is a graph illustrating the relationship between the flow rate during injection and variance for a system of the type of FIG. 1.

The lowering of flow rates during injection of the sample solution results in a significant improvement in reducing the variance of the injection, as demonstrated in FIG. 3. For this example, an injection valve with a 20 nL internal sample loop was used. The fluid flow rate for this experiment was controlled using a constant pressure pump (Jasco PU-1580) connected to a small diameter capillary that restricted the flow rate prior to the injection valve. The flow rates were determined by directly measuring the volume of fluid displaced over a fixed period of time. The injection valve used was a Valco C4 Cheminert valve with an internal sample loop volume of 20 nL (nominal specification). The variance of the injection was measured by connecting the output of the valve to a short piece of 25 micron i.d. capillary (~15 cm long). The sample plug was detected optically by measuring the absorbance versus time as the sample passed through a short section of the capillary (measurement volume of ~1 nL). The variance of the connection capillary and detection volume provided minimal dispersion and allowed a direct measurement of the variance introduced by the valve. The variance was estimated by converting the time varying absorption to volume and then fitting the distribution to a Gaussian profile. The variance of a Gaussian peak was determined as the square of its standard deviation, $\sigma$. The true variance is larger than this estimate because the fit to a Gaussian underestimates the contribution from tailing.

The variances determined for flow rates of 3.0, 1.3 and 0.54 $\mu$L/min were 1080, 530 and 280 nL$^2$ respectively. As shown in FIG. 3, the tail of the injection shows considerable dispersion and adds significantly to the variance of the injection. Further reduction in variance can be made in the system of Example 1 by using timed injections that remove much of this dispersive tail.

To achieve injection volumes of ~40 nL at 4 $\mu$L/minute would requires injection times of 0.6 seconds. In practice, even shorter times may be required to achieve desirable injection variances. Since the actuation times for most valves are in the range of 100 ms, making very reproducible injections where the valve position is changed on the 500 ms time scale is challenging. However, if the flow rate can be reduced by a factor 5–10, injection times of 2–5 seconds can be used and increased precision is possible.

EXAMPLE 2

Figure 4:
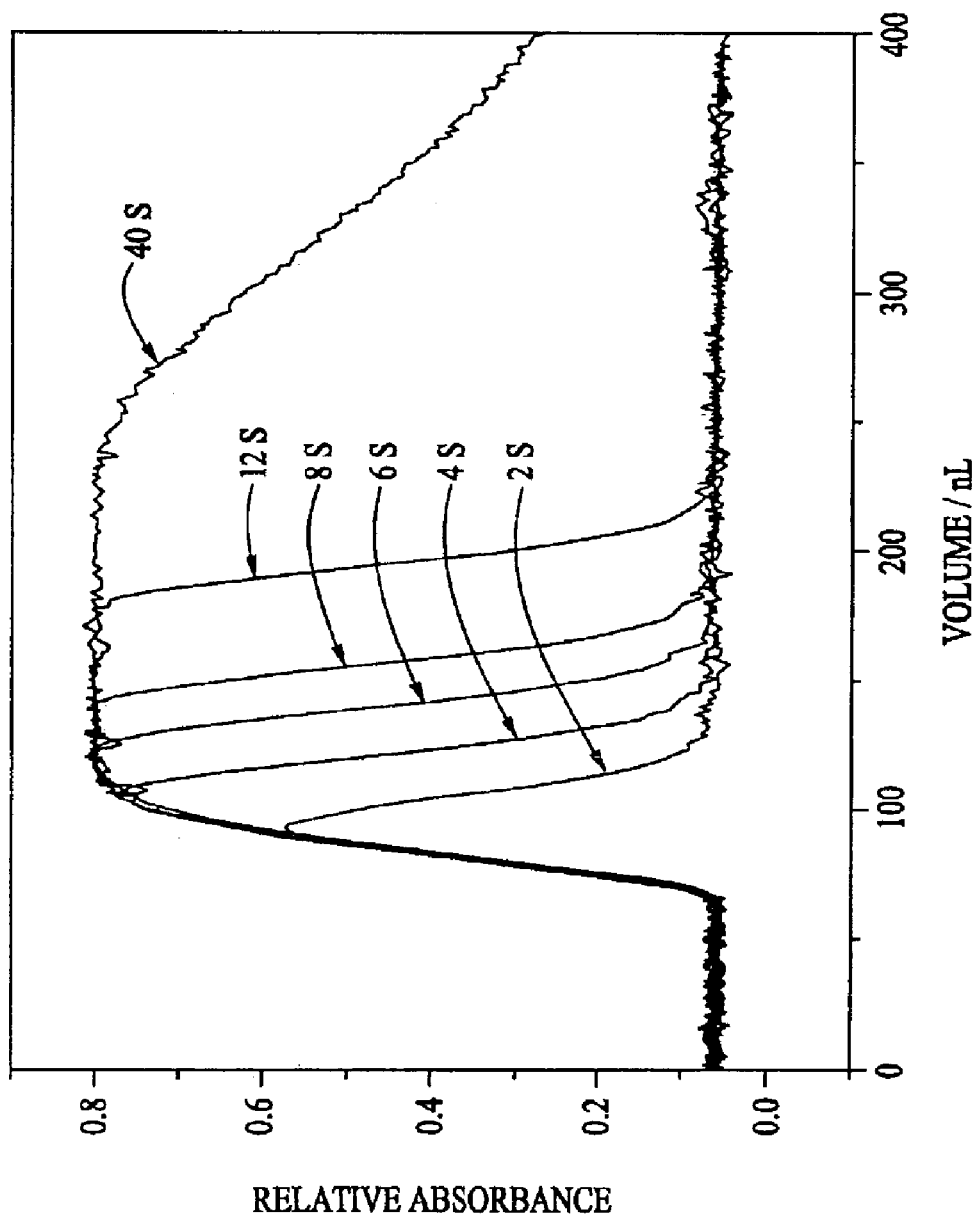
FIG. 4 is a graph illustrating the variance of timed injections at a flow rate of 540 nL/min for a system of the type of FIG. 1.

The test results for this experiment are presented in FIG. 4, which illustrates the low variance of timed injections at 540 nL/min flow rate where the injection plugs were measured as described above. The measurements used the same experimental configuration as for Example 1, except the 20 nL internal loop of the valve was changed to a ~250 nL internal loop. The valve was actuated between the load and injection positions with a standard electronic actuator available from the manufacturer (Valco).

The injection plug shapes for 2, 4, 6, 8, 12 and 40 seconds are shown and result in Full Width Half Maximum (FWHM) widths of 29, 41, 58, 112 and 270 nL. The dispersion of the measured injection plugs was characterized by the FWHM because the distributions were not well characterized by a Gaussian. The 40 second injection allowed injection of the entire loop volume and illustrates the dispersive tail from a complete loop injection. The reproducibility of peak heights was also measured. A relative standard deviation of 0.5% was measured for a series of 3 second injections at 500 nL/min followed by switching flow rates to 3 $\mu$L/min.

EXAMPLE 3

Figure 5:
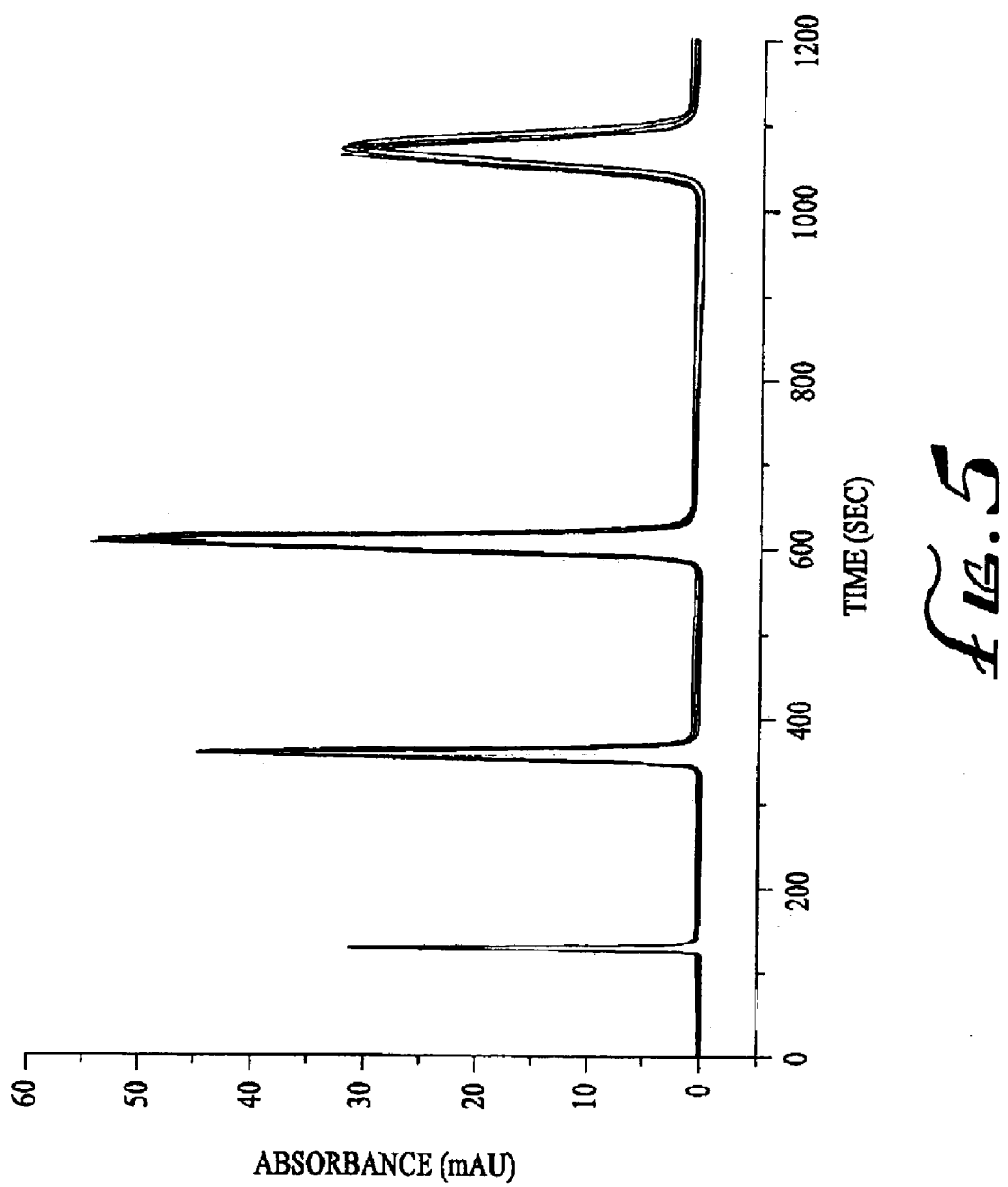
FIG. 5 is a graph of chromatographic data obtained using a system of the type illustrated in FIG. 2.

The performance of the embodiment of the invention shown in FIG. 2 has been demonstrated and the resulting test results are presented in FIG. 3. The injection valve used for this example was a Valco CN2 with a 250 nL external sample loop. The valve was pneumatically actuated under computer control. The separation column was 150 long by 0.3 mm i.d. packed with Phenomenex Luna C18 stationary phase (3 micron diameter). Detection was accomplished using a microfabricated detection cell of ~45 nL volume and a path length of ~4 mm. The relative standard deviation of peak height of <1% has been measured for 3 second injections conducted at 500 nL/min followed by switching to 4 $\mu$L/min for separation. A mixture of uracil, acetophenone, propiophenone and butyrophenone were run under isocratic conditions with a buffer of 55% methanol and 45% water. Exemplary chromatographic data is presented in FIG. 5, where the results from 9 separate separations are overlaid.

Although the present invention has been described in considerable detail with reference to certain preferred versions thereof, other versions are possible. For example, three or more variable flow rate fluid supplies can be used in a single HPLC system. In addition the working fluid used for sample injection need not be the same as the working fluid introduced into the device 18 after the sample is injected. Therefore, the spirit and scope of the appended claims should not be limited to the description of the preferred versions contained herein.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function should not be interpreted as a "means" for "step" clause as specified in 35 U.S.C. § 112.

What is claimed is:

1. A liquid chromatography system having a variable flow rate injector comprising:
   (a) an injection valve having a sample load position and a sample inject position;
   (b) a sample source;
   (c) a microcolumn having an inner diameter of two mm or less in fluid communication with the injection valve;
   (d) a variable flow rate working fluid supply in fluid communication with the injection valve and the separation column so that when the injection valve is in the sample load position a working fluid can flow into the microcolumn and sample can be placed for injection into the microcolumn, and when the injection valve is in the sample inject position the working fluid displaces placed sample for injection into the microcolumn; and
   (e) a controller in communication with the variable flow rate working fluid supply and the injection valve for controlling the flow rate of the working fluid, wherein when the working fluid displaces the sample from the injection zone, the working fluid flows at a first flow rate, and after the working fluid displaces the sample, the working fluid flows at a second flow rate and wherein the second flow rate is less than about 100 $\mu$l/min;
   wherein the first flow rate is at least 25% less than the second flow rate.

2. The system of claim 1 wherein the controller can cause the flow rate to switch from the first flow rate to the second flow rate in less than about five seconds.

3. The system of claim 1 wherein the controller can cause the flow rate to switch from the first flow rate to the second flow rate in less than about one second from the time that the valve switches from the sample inject position to the sample load position.

4. The system of claim 1 wherein the first flow rate is from about 0.01 to about 0.75 of the second flow rate.

5. The system of claim 1 wherein the controller can switch the valve between the positions; and
   wherein when the valve is in the sample inject position, the controller controls the working fluid supply to provide a selected supply of working fluid so that the working fluid displaces only a portion of the sample before the controller switches the valve to the sample load position.

6. The system of claim 1 wherein the controller can switch the valve between the positions; and
   wherein when the valve is in the sample inject position, the controller controls the working fluid supply to provide sufficient working fluid that the working fluid displaces substantially all of the sample before the controller switches the injection valve to the sample load position.

7. The system of claim 1 wherein the volume of the sample displaced is less than about 500 nL.

8. The system of claim 1 wherein the valve has an internal sample loop into which the sample can be placed.

9. The system of claim 1 comprising a sample loop external to the valve for placement of sample.

10. An HPLC system having a variable flow rate injector comprising:
    (a) an injection valve having a sample load position and a sample unload position;
    (b) a separation microcolumn in fluid communication with the injection valve;

(c) a sample source to provide a determined quantity of sample for injection into the separation column;

(d) a variable flow rate working fluid supply in fluid communication with the injection valve and the separation column so that when the injection valve is in the sample load position the working fluid flows into the separation microcolumn and when the injection valve is in the sample unload position the working fluid injects the determined quantity of sample into the separation microcolumn; and (e) a controller in communication with the variable flow rate working fluid supply and the injection valve for controlling the flow rate of the working fluid and the position of the injection valve, wherein when the working fluid injects the sample into the microcolumn, the working fluid flows at a first flow rate, and after the sample solution is injected into the microcolumn, the working fluid flows at a second flow rate, wherein the first flow rate is at least 25% less than the second flow rate and wherein the second flow rate is less than about 100 $\mu$l/min.

\* \* \* \* \*